(12) United States Patent
Seeber et al.

(10) Patent No.: US 8,604,252 B2
(45) Date of Patent: Dec. 10, 2013

(54) SUPPORTED NOBLE METAL COMPRISING CATALYST FOR OXIDATIVE DEHYDROGENATION OR EPOXIDATION

(75) Inventors: Georg Seeber, Lambsheim (DE); Peter Löchner, Worms-Rheindürkheim (DE); Stefan Bauer, Sinsheim (DE); Tobias Rosendahl, Mannheim (DE); Torsten Mäurer, Lambsheim (DE); Günter Wegner, Römerberg (DE); Martin Kamasz, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/381,807

(22) PCT Filed: Jun. 7, 2010

(86) PCT No.: PCT/EP2010/057911
§ 371 (c)(1),
(2), (4) Date: Dec. 30, 2011

(87) PCT Pub. No.: WO2011/000668
PCT Pub. Date: Jan. 6, 2011

(65) Prior Publication Data
US 2012/0108831 A1    May 3, 2012

(30) Foreign Application Priority Data
Jul. 2, 2009 (EP) .................................. 09164422

(51) Int. Cl.
C07C 45/00 (2006.01)
C07D 301/03 (2006.01)
B01J 21/10 (2006.01)
B01J 23/38 (2006.01)

(52) U.S. Cl.
USPC ........... 568/471; 568/473; 549/534; 502/243; 502/347

(58) Field of Classification Search
USPC ........... 568/471, 473; 502/243, 347; 549/534
See application file for complete search history.

(56) References Cited

U.S. PATENT DOCUMENTS

| 4,165,342 A | 8/1979 | Dudeck et al. |
| 4,816,606 A | 3/1989 | Brenner et al. |
| 5,149,884 A | 9/1992 | Brenner et al. |
| 6,013,843 A | 1/2000 | Aquila et al. |
| 6,692,713 B2 * | 2/2004 | Grunwaldt et al. ........ 423/245.1 |
| 2011/0015446 A1 | 1/2011 | Maurer et al. |

FOREIGN PATENT DOCUMENTS

| DE | 20 20 865 A1 | 11/1971 |
| DE | 27 15 209 A1 | 10/1978 |
| DE | 4010182 A1 | 10/1991 |
| DE | 10 2008 014 910.1 | 9/2009 |
| EP | 0112261 A1 | 6/1984 |
| EP | 244632 A2 | 11/1987 |
| EP | 357292 A1 | 3/1990 |
| EP | 619 142 A1 | 10/1994 |
| EP | 0881206 A1 | 12/1998 |
| EP | 1209121 A1 | 5/2002 |
| EP | 2276562 A1 | 1/2011 |
| GB | 940710 A | 10/1963 |
| GB | 1338698 A | 11/1973 |

OTHER PUBLICATIONS

Search Report for PCT/EP2010/057911 mailed Aug. 24, 2010.
Abad, A., et al., "Catalyst Parameters Determining Activity and Selectivity of Supported Gold Nanoparticles for the Aerobic Oxidation of Alcohols: The Molecular Reaction Mechanism," *Chem. Eur. J.*, 2008, vol. 14, pp. 212-222.

* cited by examiner

*Primary Examiner* — Sikarl Witherspoon
(74) *Attorney, Agent, or Firm* — Novak Druce Connolly Bove — Quigg LLP

(57) ABSTRACT

Supported noble metal-comprising catalysts which can be obtained by
a) application of colloidal noble metal in the form of a colloidal solution, optionally in admixture with additives acting as promoters, to a support material,
b1) drying of the resulting product at from 150 to 350° C., or
b2) drying of the resulting product at from 150 to 350° C. and subsequent calcination at from 350 to 550° C.
for epoxidation or oxidative dehydrogenation, a process for producing it, its use and also the use of colloidal noble metal for producing supported catalysts.

13 Claims, No Drawings

SUPPORTED NOBLE METAL COMPRISING CATALYST FOR OXIDATIVE DEHYDROGENATION OR EPOXIDATION

CROSS-REFERENCE TO RELATED APPLICATIONS

This application is a national stage application (under 35 U.S.C. §371) of PCT/EP2010/057911, filed Jun. 7, 2010, which claims benefit of European application 09164422.9, filed Jul. 2, 2009.

The present invention relates to a supported noble metal catalyst, a process for producing it and also its use for epoxidation or oxidative dehydrogenation, in particular for preparing olefinically unsaturated carbonyl compounds from olefinically unsaturated alcohols by oxidative dehydrogenation.

The present invention further relates to the novel use of colloidal noble metals for producing supported noble metal-comprising catalysts, in particular for epoxidation or oxidative dehydrogenation.

In particular, the present invention relates to the use of supported noble metal catalysts which can be obtained by a particular process for preparing 3-methylbut-2-en-1-al (MBA) from 3-methylbut-3-en-1-ol (MBE).

The preparation of alpha-beta-unsaturated carbonyl compounds by oxidative dehydrogenation over suitable catalysts is known to those skilled in the art and has been widely described in the literature.

Accordingly, DE-B-20 20 865 describes a process for preparing alpha-beta-unsaturated carbonyl compounds, in which, according to the description, alloys and metal compounds, especially some metal oxides of the transition elements can be used as dehydrogenation catalysts. Furthermore, this document states that the catalysts can be used in pure form or in the form of mixed catalysts with or without a support substance. Zinc oxide, cadmium oxide and manganese oxide and also mixed catalysts comprising the metals Cu, Ag and/or Zn are mentioned as being particularly suitable. No further information on the production of the catalyst is to be found in this document.

EP-A 881 206 describes a process for the continuous industrial preparation of unsaturated aliphatic aldehydes in a shell-and-tube reactor. Preferred catalysts for this process are said to be supported silver catalysts which comprise spheres of an inert support material coated with from 0.1 to 20% by weight, based on the amount of the support, of a layer of metallic silver in the form of a smooth, abrasion-resistant shell. Furthermore, a particular ratio of the largest diameter of the coated catalyst spheres to the internal diameter of the reaction tube should preferably be adhered to.

DE-A 27 15 209 discloses a process for preparing 3-alkylbuten-1-als, in which a catalyst having a total layer thickness of from 5 to 35 mm and 2 or more layers of silver and/or copper crystals is used. The production of the catalyst having a plurality of layers of the noble metal is relatively complicated.

EP-A 357 292 discloses a process for preparing ethylene oxide. Catalysts used in this process are silver catalysts in which the silver has been applied to a porous heat-resistant support having a particular specific surface area determined by the BET method. According to the information in this document, the silver can be applied as a suspension of silver or silver oxide in a liquid medium, for example water, to the support or by impregnation of the support with a solution of a silver compound. This silver compound is subsequently reduced to elemental silver by thermal treatment. This document gives no pointers to the possible use of the silver-comprising supported catalysts produced in this way for preparing ethylenically unsaturated carbonyl compounds, nor to possible uses of colloidal silver.

EP-A 619 142 discloses silver catalysts for the oxidation of ethylene to ethylene oxide, which catalysts are obtained by impregnation with an aqueous (colloidal) solution of a silver salt; pointers to possible uses of colloidal silver are not given by this document.

Furthermore, the German patent application DE 10 2008 014 910.1, which is not a prior publication, discloses noble metal-comprising catalysts which are obtained by application of a complexed sparingly soluble compound of a noble metal from suspension or solution to a support and subsequent thermal treatment.

All documents cited in the present application are incorporated by reference in their entirety into the present disclosure.

3-Methylbut-2-en-1-al, also known under the trivial name prenal, is an important precursor for citral which is in turn an important starting material for many chemical syntheses. The catalysts described in the literature for preparing prenal (MBA, 3-methylbut-2-en-1-al) are produced by relatively complex processes and under production conditions which are overall in need of improvement. It would therefore be desirable to have noble metal-comprising supported catalysts for the synthesis of prenal from isoprenol (MBE, 3-methylbut-3-en-1-ol) which can be obtained in a simple way and whose selectivity can be controlled in a simple way by addition of compounds which act as promoters.

Furthermore, it would also be desirable to have catalysts for the preparation of ethylene oxide from ethylene which are simple to produce and give very good yields, conversions, selectivities, etc.

SUMMARY OF THE INVENTION

It was accordingly an objet of the present invention to counter the disadvantages and requirements arising from the prior art and make available appropriate catalysts and production processes for these and uses.

According to the invention, this object is achieved by supported noble metal-comprising catalysts which are produced by application of colloidal noble metal in the form of a colloidal solution, optionally in admixture with additives acting as promoters, to a support material and subsequent thermal treatment of the product obtained.

The present invention further provides, in a further aspect to achieve the object, a process for producing this supported noble metal-comprising catalyst for epoxidation or oxidative dehydrogenation, wherein colloidal noble metal in the form of a colloidal solution, optionally in admixture with additives acting as promoters, to a support material and the product obtained is subsequently subjected to a thermal treatment.

The present invention likewise provides, in further aspect to achieve the object, for the use of the supported noble metal-comprising catalysts which are produced by application of colloidal noble metals in the form of a colloidal solution, optionally in admixture with additives acting as promoters, to a support material and subsequent thermal treatment of the product obtained for epoxidation or oxidative dehydrogenation, in particular for the preparation of olefinically unsaturated carbonyl compounds from olefinically unsaturated alcohols by oxidative dehydrogenation.

Last but not least, the present invention provides the novel use of colloidal noble metals for producing supported noble metal-comprising catalysts by application of colloidal noble metal.

For the purposes of the present invention, all amounts are, unless indicated otherwise, by weight.

For the purposes of the present invention, the term "room temperature" refers to a temperature of 23° C. Temperatures indicated are, unless indicated otherwise, in degrees celsius (° C.).

Unless indicated otherwise, the reactions or process steps described are carried out at atmospheric pressure.

Spherical means, for the purposes of the present invention, that the primary particles concerned are spheroidal and do not display any preferential direction or edges in transmission electron microscopy (TEM), comparable to ideal spheres.

The term "thermal treatment" refers, for the purposes of the present invention, to
a) drying or
b) drying and calcination.

For the purposes of the present invention, the term colloid refers to particles which are finely dispersed in a solvent. The average particle size of a colloid is in the range from about 1 nm (nanometer) to 10 000 nm (10 microns). In the case of spherical colloids, the average particle size means the weight average particle size; in the case of colloids which do not have a spherical shape, the particle size indicated can also relate to only one dimension (e.g. in the case of platelet-like colloids).

In terms of their properties, colloidal solutions are between genuine (molecularly disperse) solutions and suspensions (coarsely disperse solutions) and in terms of their properties come closer to genuine solutions, the smaller the average particle size of the colloid.

Colloidal solutions accordingly differ in terms of their properties from suspensions.

The weight average particle size can be determined by means of an analytical ultracentrifuge using the method of W. Scholtan and H. Lange, Kolloid-Z. and Z.-Polymers 250 (1972), pages 782 to 796. The ultracentrifuge measurement gives the integrated mass distribution of the particle diameter of a sample. From this it is possible to determine the percentage by weight of the particles which have a diameter equal to or smaller than a particular size. The average particle diameter, also referred to as D50 of the integrated mass distribution, is defined as the particle diameter at which 50% by weight of the particles have a diameter smaller than the diameter corresponding to the D50. Likewise, 50% by weight of the particles then have a diameter greater than the D50.

Colloidal systems display, owing to their above-average surface area to volume ratio, pronounced effects of surface and interface chemistry.

The interactions between the individual colloid particles in a colloidal system can be influenced within a wide range by choice of the particles, treatment of the surface and the composition of the liquid.

For the purposes of the present invention, colloidally dissolved noble metals, i.e. colloidal solutions of noble metals, are used in the production of supported catalysts.

The supported noble metal-comprising catalysts of the invention have a specific resistance measured at 23° C. of not more than 1000 ohm meter ($\Omega$*m), preferably not more than 500 ohm meter ($\Omega$*m) and particularly preferably not more than 100 ohm meter ($\Omega$*m).

The specific resistance is, for the purposes of the present invention, determined in a measurement cell whose bottom comprises stainless steel and whose wall comprises insulating plastic (internal diameter 10 mm, height 32 cm, catalyst volume about 25 ml). The catalyst is introduced and tapped a little in order to achieve a uniform catalyst bed. A stainless steel punch is then placed on the catalyst bed. Punch and bottom serve as measurement electrodes in this measurement arrangement. To measure the resistance, a current measuring instrument is connected in series with the sample and a voltage in the range from 10 mV and 5 V is set by means of a maze device. The associated current is recorded and the specific resistance is calculated. The measurement is carried out at atmospheric pressure and an atmospheric humidity of not more than 50% at a temperature of 23° C.

Preferred embodiments of the invention may be found in the dependent claims and the following description and the examples.

In the use according to the invention, a supported noble metal-comprising catalyst which can be obtained by applying colloidal noble metal in the form of a colloidal solution, optionally in admixture with additives acting as promoters, to a support material and subsequently subjecting the product obtained to a thermal treatment is used.

Preference is given to using Cu, Au, Ag, Pd, Pt, Rh, Ru, W, Ir or Os or mixtures of alloys thereof as colloidal noble metals.

Particular preference is given to using Au and Ag or mixtures or alloys thereof as colloidal noble metals.

Very particular preference is given to the use of colloidal silver.

Colloidal gold and colloidal silver have been known for a long time and are described in the literature.

Colloidal silver was in the past also used therapeutically for combating infection before more effective agents were available. Such products are sometimes also referred to as silver sol or silver water in the literature.

In general, colloidal silver is a liquid system of elemental silver or sparingly soluble silver compounds, preferably elemental silver, in a solvent having particle sizes in the range from 1 to 100 nm, preferably from 10 to 80 nm (nanometers), where the particle sizes relate to elemental silver or silver compounds. The individual colloid particles comprise from about 1000 to 1 000 000 000 silver atoms or molecules of the respective silver compound.

Colloidal silver can be produced, for example, by mechanical milling in colloid mills, by means of various electrolytic processes (for example deposition from electrodes) or by means of chemical processes (for example the reduction of particular silver compounds).

Colloidal gold or other colloidal noble metals can be produced in an analogous way by replacing silver or silver salts by gold or gold salts or by the respective other noble metals or salts thereof.

It is in principle also possible to use mixtures of various noble metals in the form of their colloidal solutions, but in this case interactions between the colloid particles which are difficult to foresee and may cause undesirable effects occur. Preference is therefore given to colloidal solutions of one of the abovementioned noble metals.

Suitable colloidal noble metals of the above-described type are commercially available (e.g. Sigma-Aldrich, VWR, Fluka), with the range of products for colloidal silver and colloidal gold being the most comprehensive.

The colloidal noble metal particles are introduced into the solvent by adding them to the solvent and then dispersing them by stirring. This can preferably be carried out at room temperature and atmospheric pressure; however, it is likewise possible to adapt temperature and pressure to the respective requirements.

In one variant of the present invention, organic solvents, in particular $C_1$-$C_6$-alkanols, dimethyl sulfide, dimethyl sulfoxide, N-methylformamide, dimethylformamide, tetrahydrofuran, acetone, benzene, toluene, can be used.

In a further variant, it is possible to use water-miscible solvents, in particular preferably water-miscible solvents such as acetone, $C_1$-$C_6$-alkanols, dimethyl sulfoxide, dimethylformamide, tetrahydrofuran, N-methylformamide, in admixture with water as solvent.

For the purposes of the present invention, water is most preferably used as solvent for the colloidal noble metals.

The noble metals are preferably present in solutions from which they are applied to the support material in proportions, calculated as noble metal based on the total solution, in the range from 5 to 35% by weight, preferably in the range from 10 to 30% by weight and particularly preferably in the range from 15 to 25% by weight.

Further additives suitable as promoters can be added to this solution of the colloidal noble metals. Merely by way of example, mention may here be made of alkali metals, alkaline earth metals and transition metals (e.g. Li, Rb, Cs, Ca, Mg, V, Co, Ni, Ir or Re), which can be used, for example, as halides (fluorides, chlorides), carboxylates or nitrates or else in the form of sulfur-comprising anions such as sulfates, sulfites or sulfides. Phosphates, cyanides and hydroxides and also carbonates or mixtures thereof are likewise suitable. Finally, it is also possible to use anions of heteropolyacids, in particular heteropolyacids of the elements of transition groups six and seven of the Periodic Table (notation according to the IUPAC proposal of 1985). The abovementioned promoters can also be introduced separately from the colloidal solutions of the noble metals. The way in which such promoters are used in supported catalyst systems are known per se to those skilled in the art and are described in the literature, so that further details are superfluous here.

Suitable support materials are known per se to those skilled in the art and are partly commercially available from for example, CeramTec, Saint-Gobain Norpro and are also described in the literature, to which reference is made here for further details.

Preferred support materials are steatite, aluminum oxides or aluminosilicates. Particularly suitable supports are those which are present is spherical form, with the spherical support particles having an average diameter in the range from 0.5 to 3 mm. According to the invention, preference is given to using support material in spherical form, with the spherical support particles having an average diameter in the range from 0.5 to 1.5 mm, for the reaction of MBE to form MBA, while the support materials preferably have the shape of hollow rings for epoxidation, in particular of ethylene. Preference is given to geometries of 5-10×5-10×2-5 mm, in particular 6×6×3 or 8×8×3 mm (external diameter times length times hole diameter of the hollow ring).

The precise size of the supports is nonetheless not critical for the present invention.

In a preferred embodiment of the present invention, the support materials for the reaction of MBE to form MBA have a very low porosity and have a BET surface area of not more than 1 $m^2$/g, preferably not more than 0.5 $m^2$/g, and in a particularly preferred embodiment comprise steatite.

In a preferred embodiment of the present invention, the support materials for epoxidation, in particular of ethylene, have a very low porosity and have a BET surface area of less than 10 $m^2$/g, preferably less than 3 $m^2$/g and particularly preferably less than 1 $m^2$/g, and, in a particularly preferred embodiment, comprise $Al_2O_3$.

The BET surface area of the supports which can be used according to the invention can be so low that it is down to 0.01 $mm^2$/g, or down to 0.001 $m^2$/g.

In some cases, hydrotalcites have been found to be suitable.

Hydrotalcite is generally understood to be a sheet material having the chemical formula $[M(II)_xM(III)_{1-x}(OH)_2]^{(1-x)+}[A_{1-X/n}]^{(1-x)-}*m H_2O$. Here, M(II) is a divalent metal, M(III) is a trivalent metal, A is an anion incorporated in the lattice, n is the valence of the anion, m is the number of incorporated water molecules and x is the molar ratio of M(II)/[M(II)+M(III)]. It is usual for x to be in the range from 0.2 to 0.33, which corresponds to molar ratios of M(III) to M(II) in the range from 2 to 4. As divalent metals, mention may here be made by way of example of Mg, Fe, Ni, Co, Zn and Mn, and as trivalent metals, mention may be made of Al, Ga, In, Co and Mn. The possible simultaneous presence of a plurality of divalent or trivalent metals in different molar ratios increases the structural variety of the suitable hydrotalcites.

As minerals of the hydrotalcite group, mention may here be made, purely by way of example, of manasseite, pyroaurite, sjögrenite, stichtite, barbertonite, desautelsite, meixnerite or takovite, which are described in the literature and whose compositions are known to those skilled in the art. A preferred hydrotalcite has the composition $Mg_6Al_2(CO_3)(OH)_{16}*4H_2O$.

A particularly preferred support material is steatite, a ceramic material based on natural raw materials which comprises the main component soapstone $(Mg(Si_4O_{10})(OH)_2)$, a natural magnesium silicate. Additions of clay and feldspar or barium carbonate can also be comprised.

A further preferred support material is alpha-aluminum oxide.

The production of the noble metal-comprising catalysts according to the present invention comprises the following steps:

a) application of colloidal noble metal in the form of a colloidal solution, optionally in admixture with additives acting as promoters, to a support material, b1) drying of the resulting product at from 150 to 350° C., or b2) drying of the resulting product at from 150 to 350° C. and subsequent calcination at from 350 to 550° C., where step a) can comprise the substeps a1) mixing of the support material with colloidally dissolved noble metal, a2) optionally ageing of the resulting mixture by allowing it to stand for a period of from 1 to 90 minutes, preferably from 30 to 60 minutes, particularly preferably from 40 to 50 minutes, optionally with continuous or intermediate stirring, a3) isolation of the resulting product, preferably by filtration and/or evaporation.

The ageing which is optionally carried out in step a2) is optionally carried out when the property changes resulting therefrom are desirable.

The evaporation optionally carried out in step a3) represents predrying and generally takes place at temperatures in the range from 15 to 80° C. and under normal atmospheric pressure. The evaporation can be carried out together with filtration.

It is possible for the purposes of the present invention to allow steps a3) and b1) or b2) to go over into one another continuously, so that no delay time occurs between these steps.

However, it is likewise possible to have a delay time between these steps. However, the duration of the delay time is not critical and is determined merely by the practical circumstances in each case. In a preferred embodiment, it is in the range from 1 to 120 minutes.

The alternatives indicated in steps b1) and b2) will for the purposes of the present invention also be described by the collective term "thermal treatment".

In step b2), a delay time can be inserted between the individual steps "drying" and "calcination". However, the duration of the delay time is not critical and is determined merely by the practical circumstances in each case. It is preferably in the range from 1 to 300 minutes.

In a variant of the present invention, it is possible to store the product after drying and calcine it only after any desired period of time (even after months); the catalyst performance is not impaired thereby.

In one variant of the present invention, it is possible to allow the steps "drying" and "calcination" mentioned in step b2) to go over into one another continuously or to heat the product obtained in step a) directly to the calcination temperature so that drying occurs effectively in a "quick pass".

The variant of step b1) is employed in a preferred embodiment when the catalyst is to be used for epoxidation, in particular for preparing ethylene oxide from ethylene.

The variant of step b2) is employed in another preferred embodiment when the catalyst is to be used for oxidative dehydrogenation, in particular the preparation of MBA from MBE.

In a variant of the present invention, the preparation does not comprise any further steps but consists of those mentioned.

This preparative process relates both to the noble metal-comprising catalysts of the invention and to the use according to the invention for producing the noble metal-comprising catalysts and of course to the process of the invention.

After application of the colloidal noble metal, optionally with addition of promoters, from solution to the support material, the latter is subjected, in a first variant of the invention, to drying at temperatures in the range from 150 to 350° C., preferably from 200 to 300° C. and particularly preferably from 225 to 285° C.

In a second variant of the invention, after application of the colloidal noble metal, optionally with addition of promoters, from solution to the support material, the latter is subjected to drying at temperatures in the range from 150 to 350° C., preferably from 200 to 300° C. and particularly preferably from 225 to 285° C. and subsequently calcination at temperatures in the range from 350 to 550° C., preferably from 400 to 500° C. and particularly preferably from 425 to 475° C.

In both variants, drying is preferably carried out for a time in the range from 2 to 45 minutes, preferably from 5 to 30 minutes and particularly preferably from 10 to 20 minutes.

Calcination is preferably carried out for a time in the range from 15 minutes to 3 hours, preferably from 30 minutes to 2 hours and particularly preferably from 45 to 90 minutes.

Drying is preferably carried out under conventional auxiliary conditions, i.e. at atmospheric pressure (or a low gauge pressure due to the apparatus—the introduction of gas into the apparatus leads to a small backpressure, generating the pressure in the apparatus) under a nitrogen, noble gas or air atmosphere, preferably air atmosphere. Calcination is preferably carried out under conventional conditions, i.e. at atmospheric pressure (or a low gauge pressure due to the apparatus—the introduction of gas into the apparatus leads to a small backpressure, generating the pressure in the apparatus) under a nitrogen, noble gas or air atmosphere, preferably air atmosphere.

As a result of the thermal treatment, a coating of noble metal itself is formed on the surface of the support material, including the internal surface area of the pores, from the colloidal noble metal and this noble metal coating then represents the active species of the supported catalyst.

The noble metal contents, measured in % by weight based on the catalyst (i.e. support plus noble metal), after the thermal treatment are generally in the range from 0.5 to 40% by weight, preferably in the range from 0.8 to 30% by weight and particularly preferably in the range from 1.7 to 20% by weight.

It has in some cases been found to be advantageous for different supports to have different contents of noble metal.

When the catalyst is to be used for oxidative dehydrogenation, in particular for preparing MBA from MBE, preference is given, according to the invention, to the noble metal contents being in the range from 0.5 to 6.0% by weight, in particular from 0.8 to 3% by weight, based on the catalyst.

When the catalyst is to be used for epoxidation, in particular for preparing ethylene oxide from ethylene, preference is given, according to the invention, to the noble metal contents being in the range from 5 to 40% by weight, in particular from 10 to 30% by weight, based on the catalyst.

When, in particular, steatite having a BET surface area of less than 1 $m^2/g$ is used as support material, the noble metal content, based on the catalyst, is preferably in the range from 0.5 to 2.5% by weight, particularly preferably in the range from 0.8 to 2.2% by weight and in particular in the range from 1.7 to 2.2% by weight.

When, in particular, alpha-aluminum oxide having a BET surface area of less than 10 $m^2/g$ is used as support material, the noble metal content, based on the catalyst, is preferably in the range from 5 to 40% by weight, particularly preferably in the range from 10 to 30% by weight and in particular in the range from 13 to 20% by weight.

A person skilled in the art can, on the basis of knowledge of the field, vary the precise content of the noble metal by means of simple measures such as noble metal content of the colloidal solution, residence time of the support in the colloidal solution and size and nature of the support and match them to the respective task.

For example, in the case of porous supports the water absorption into the pores of the support material can play a role and the impregnation solution can be tailored to the support, while in the case of nonporous supports the noble metal content can be controlled mainly via the concentration and viscosity of the impregnation solution.

According to the invention, the supported noble metal-comprising catalysts which can be obtained by the abovementioned procedure can particularly advantageously be used for preparing 3-methylbut-2-en-1-al from 3-methylbut-3-en-1-ol. The product is also known by the trivial name prenal (MBA), and the starting material is known under the trivial name isoprenol (MBE).

In this particularly preferred use, the reaction is preferably carried out in a shell-and-tube reactor as described, for example, in EP-A 881 206 A1. For further details of the reactor geometry, explicit reference may be made here to EP-A 881 206 A1, page 2, lines 37 to 45 and page 5, lines 40 to 43, and EP-A 244 632 A2, FIGS. 1 to 3.

The use according to the invention of the noble metal-comprising supported catalysts which can be obtained as described above makes it possible to obtain prenal from isoprenol in good yield and with good selectivity under mild temperature conditions. The reaction of isoprenol with the noble metal-comprising supported catalyst which can be obtained as described above forms a reaction mixture composed of 3-methylbut-3-en-1-al (IMBA) and 3-methylbut-2-en-1-al (MBA).

In the work-up of the reaction mixture, the desired reaction product is separated by distillation from unreacted starting material in a first stage. To be able to carry out this distillation in an economically advantageous way, it is advantageous to make use of an azeotrope which comprises 70% of 3-methylbut-3-en-1-al and 30% of 3-methylbut-2-en-1-al.

The use according to the invention of the supported noble metal-comprising catalyst which can be obtained as described above enables prenal to be prepared in good yield at low temperatures and with good selectivity from isoprenol.

Within the framework of the present invention, it is possible, for example, to achieve yields of greater than 45%, in particular 48% and more, and selectivities of greater than 75%, in particular 80% and more, in, for example, the reaction of MBE to form MBA at temperatures of from 350 to 385° C.

In a further advantageous variant, the supported noble metal-comprising catalysts which can be obtained by the above procedure can, according to the invention, be used for the preparation of ethylene oxide from ethylene.

Within the framework of the present invention, it is possible to achieve yields of from 5 to 10%, in particular greater than 6% (e.g. 6.7%), for example from 6 to 8%, in a single pass and selectivities of greater than 70%, in particular from 73 to 82% and more, in, for example, the epoxidation of ethylene to ethylene oxide at temperatures of from 245 to 270° C.

Of course, the catalysts of the invention can also be used for reactions other than those mentioned, in particular for oxidations in general.

Accordingly, the present invention also comprises the use in general of the catalysts of the invention for oxidation reactions.

The present invention further comprises the use of colloidal noble metals for producing supported noble metal-comprising catalysts, in particular supported noble metal-comprising catalysts for epoxidation or oxidative dehydrogenation.

For this use, all noble metals mentioned above and also any support materials, preferably those mentioned above, are possible. This use is not tied to the production process described above, even though this is preferred.

An advantage of the present invention is accordingly that the production of the catalysts can be controlled (varied) very simply and well. A further advantage is that very good yields and selectivities are achieved by means of the catalysts of the invention.

A further advantage of the present invention is that catalysts which even when the amount of gas is increased significantly by 10 or even 20% display no deterioration in performance but give a constant selectivity and conversion are obtained.

In a less preferred but possible variant of the present invention, epoxidation and oxidative dehydrogenation can be carried out simultaneously.

It is of course possible to use the catalysts of the invention both in processes which are carried out in a single pass and also in processes carried out in the recycle mode.

The various embodiments of the present invention, e.g. those of various dependent claims, can be combined with one another in any way.

The invention will now be illustrated with reference to the following nonlimiting examples.

EXAMPLES

Example 1

Production of a Solution of Colloidal Silver 30.02 g of colloidal silver (Fluka, catalogue No.: 85131) were added a little at a time while stirring to 120.01 g of distilled water and stirred for another 1 hour. A greenish brown, colloidal solution having a proportion by mass of about 13.8% by weight of silver was formed.

Example 2

Production of a Supported Catalyst According to the Invention 100 g of steatite spheres having an average diameter of 1.8-2.2 mm (from Ceramtec) were placed in a 250 ml glass beaker. 37.0 g of the colloidal silver solution produced as per example 1 were subsequently added and mixed in with a spatula. After allowing it to stand for 45 minutes with occasional stirring by means of the spatula, the coated spheres were transferred to a square mesh having an edge length of 21.5 cm, mesh opening of 1.5 mm, and dried in an oven (Horo, model 112) at 250° C. for 12 minutes under a stream of air of 8 $m^3$/h and a gauge pressure of 1 mbar gauge above atmospheric pressure due to the apparatus. The coated steatite spheres were subsequently calcined at 450° C. for one hour in air in a muffle furnace (Nabertherm) and then cooled to room temperature again.

The amount of active composition applied to the catalyst was 1.96%.

Example 3

Catalyst Testing—Preparation of Prenal

A bed of 10 ml of the catalyst produced as per example 2 was introduced into a fused silica reactor. The reaction, (preparation of 3-methylbut-2-en-1-al from 3-methylbut-3-en-1-ol) was then carried out by vaporizing 110 g/h of MBE and 50 l/h of air by means of a thin film evaporator, with the temperature being set so that the MBE conversion was 60%.

The colloidal silver catalyst displayed stable performance data of 60% MBE conversion at 80% selectivity to MBA+ IMBA and yields of 48% over an operating time of 1800 hours and over many burning-off cycles and also an increase in the GHSV (gas hourly space velocity) by 10% and by 20%.

The catalyst produced as per example 2 is therefore significantly superior to the conventional catalyst by means of which yields of only 45% can be achieved.

Example 4

Catalyst Testing—Preparation of Ethylene Oxide

A supported catalyst was firstly produced in a manner analogous to examples 1 and 2 above by depositing colloidal silver solution comprising salts of various promoters on alpha-aluminum oxide as support material, with the catalyst being thermally treated at 280° C. for 12 minutes and not after-calcined. A supported catalyst having a content of 15.5% by weight of silver and modified by means of various promoters (Li—175 ppm, Cs—430 ppm, W—140 ppm, Re—270 ppm, S—38 ppm) was obtained.

As tube reactor, use was made of a double-wall reactor made of stainless steel and having an internal diameter of 6 mm. The length of the tube reactor was 2200 mm. 29.2 g of crushed supported catalyst having a particle size of from 0.6 to 0.9 mm were used as catalyst bed. The length of the bed was about 110 cm.

A reaction gas feed mixture having the following composition:

| | |
|---|---|
| 35% by volume | of ethylene, |
| 7% by volume | of molecular oxygen, |
| 1% by volume | of carbon dioxide, |
| 0.15% by volume | of water, |
| 2.6 - 2.9 ppm by volume | of ethyl chloride (moderator) and methane as balance to 100% by volume was introduced into the reaction space, following from the top downward. |

The admission pressure of the reaction gas mixture on entry into the reaction space was 16 bar absolute. The space velocity of the reaction gas feed mixture through the about 110 cm long crushed catalyst bed was 4750 $h^{-1}$. As heat transfer medium, a heat transfer oil of the type AP 100 silicone oil from Wacker Chemie, Munich, was conveyed through the intermediate space between the two walls. The heat transfer oil was introduced at the lower end of the tube reactor at an entry temperature $T_W^{in}$ and flowed from the bottom upward where it flowed out from the space between the double wall, $T_W^{in}$ was selected and continuously adapted so that the ethylene oxide content of the reaction gas mixture leaving the reaction space was always 2.7% by volume. The ethylene chloride content of the reaction gas feed mixture was increased over the running time so that the maximum selectivity of ethylene oxide target product formation was achieved at any point in time during operation.

After 150 hours of operation, the following experimental result was obtained: $T_W^{in}=252°$ C.; $S^{ethylene\ oxide}=74\%$ ($S^{ethylene\ oxide}$=selectivity to ethylene oxide).

The invention claimed is:

1. A process for producing a supported noble metal-comprising catalyst for epoxidation or oxidative dehydrogenation, which comprises
    a) applying colloidal silver in the form of a colloidal solution, optionally in admixture with additives acting as promoters, to a support material comprising steatite,
    b1) drying the product obtained at from 150 to 350° C., or
    b2) drying the product obtained at from 150 to 350° C. and subsequently calcining at from 350 to 550° C.

2. The process according to claim 1, wherein a supported noble metal-comprising catalyst for the oxidative dehydrogenation of olefinically unsaturated alcohols is produced.

3. The process according to claim 1, wherein step a) comprises the substeps
    a1) mixing of the support material with colloidally dissolved silver,
    a2) optionally ageing of the resulting mixture by allowing it to stand for a period of from 1 to 90 minutes, optionally with continuous or intermediate stirring,
    a3) isolating the resulting product.

4. The process according to claim 1, wherein step a) comprises the substeps
    a1) mixing of the support material with colloidally dissolved silver,
    a2) optionally ageing of the resulting mixture by allowing it to stand for a period of from 1 to 90 minutes, optionally with continuous or intermediate stirring,
    a3) isolating the resulting product by filtration and/or evaporation.

5. A supported noble metal-comprising catalyst which is obtained by
    a) applying colloidal silver in the form of a colloidal solution, optionally in admixture with additives acting as promoters, to a support material comprising steatite,
    b1) drying of the resulting product at from 150 to 350° C., or
    b2) drying of the resulting product at from 150 to 350° C. and subsequent calcining at from 350 to 550° C.

6. The catalyst according to claim 5, wherein the support material is a basic or acidic support material.

7. A process for producing a supported noble metal-comprising catalyst for epoxidation or oxidative dehydrogenation, which comprises
    a) applying colloidal silver in the form of a colloidal solution, optionally in admixture with additives acting as promoters, to a support material comprising steatite to form a product,
    b2) calcining the product at a calcination temperature of from 350 to 550° C., wherein the product is directly heated to the calcination temperature.

8. The process according to claim 7, wherein a supported noble metal-comprising catalyst for the oxidative dehydrogenation of olefinically unsaturated alcohols is produced.

9. The process according to claim 7, wherein step a) comprises the substeps
    a1) mixing of the support material with colloidally dissolved silver,
    a2) optionally ageing of the resulting mixture by allowing it to stand for a period of from 1 to 90 minutes, optionally with continuous or intermediate stirring,
    a3) isolating the resulting product.

10. The process according to claim 7, wherein step a) comprises the substeps
    a1) mixing of the support material with colloidally dissolved silver,
    a2) optionally ageing of the resulting mixture by allowing it to stand for a period of from 1 to 90 minutes, optionally with continuous or intermediate stirring,
    a3) isolating the resulting product by filtration and/or evaporation.

11. A supported noble metal-comprising catalyst which is obtained by the process of claim 7.

12. A process for epoxidation or oxidative dehydrogenation which comprises utilizing the supported noble metal-comprising catalyst according to claim 5.

13. A process for epoxidation or oxidative dehydrogenation which comprises utilizing the supported noble metal-comprising catalyst which is obtained by the process according to claim 7.

* * * * *